US011090162B2

(12) United States Patent
Tuttle (10) Patent No.: US 11,090,162 B2
(45) Date of Patent: Aug. 17, 2021

(54) BONE IMPLANT WITH STRUTS (71) Applicant: Wright Medical Technology, Inc., Memphis, TN (US)

(72) Inventor: David R. Tuttle, Memphis, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 223 days.

(21) Appl. No.: 16/477,008

(22) PCT Filed: Mar. 27, 2018

(86) PCT No.: PCT/US2018/024458
§ 371 (c)(1),
(2) Date: Jul. 10, 2019

(87) PCT Pub. No.: WO2018/203991
PCT Pub. Date: Nov. 8, 2018

(65) Prior Publication Data
US 2019/0350717 A1    Nov. 21, 2019

Related U.S. Application Data

(60) Provisional application No. 62/501,283, filed on May 4, 2017.

(51) Int. Cl.
*A61F 2/30* (2006.01)
*A61F 2/42* (2006.01)

(52) U.S. Cl.
CPC ...... *A61F 2/30771* (2013.01); *A61F 2/30749* (2013.01); *A61F 2/4202* (2013.01);
(Continued)

(58) Field of Classification Search
CPC .............. A61F 2/30771; A61F 2/30749; A61F 2002/30028; A61F 2002/30003;
(Continued)

(56) References Cited

U.S. PATENT DOCUMENTS 4,714,473 A    12/1987   Bloebaum et al.
8,888,862 B2   11/2014   McDonnell et al.
(Continued)

FOREIGN PATENT DOCUMENTS

CN    101862473 A    10/2010
CN    104159621 A    11/2014
(Continued)

OTHER PUBLICATIONS

International Search Report and Written Opinion issued in connection with International Patent Application No. PCT/US2018/024458, 10 pages, dated Jul. 13, 2018.
(Continued)

*Primary Examiner* — Alvin J Stewart
(74) *Attorney, Agent, or Firm* — Duane Morris LLP (57) ABSTRACT

An implant includes a component for fixed attachment to a bone. An underpass layer of a porous material is disposed on a first side of the component for fixed attachment. At least one strut is provided on the underpass layer. The at least one strut has a first surface contacting the underpass layer and a second surface opposite the first surface. The at least one strut comprises a non-porous material. An additional layer of the porous material fills a respective volume adjacent the at least one strut. The additional layer extends from a first side of the underpass layer to a predetermined height at or above the second surface of the at least one strut.

17 Claims, 11 Drawing Sheets

(52) U.S. Cl.
CPC .............. *A61F 2002/30011* (2013.01); *A61F 2002/30387* (2013.01); *A61F 2002/30784* (2013.01); *A61F 2002/30879* (2013.01); *A61F 2002/30892* (2013.01); *A61F 2002/30985* (2013.01); *A61F 2002/4205* (2013.01); *A61F 2002/4207* (2013.01)

(58) Field of Classification Search
CPC .. A61F 2002/30011; A61F 2002/30769; A61F 2/30767; A61F 2002/30784; A61F 2002/30892; A61F 2/4202; A61F 2002/4205; A61F 2002/4207; A61F 2002/421; A61F 2250/0024; A61F 2250/0026; A61F 2250/0023; A61F 2002/2835
See application file for complete search history.

(56) References Cited

U.S. PATENT DOCUMENTS

| | | | |
|---|---|---|---|
| 9,055,977 | B2 | 6/2015 | Jiang et al. |
| 10,213,309 | B2 * | 2/2019 | Lindsey ................ A61B 17/68 |
| 2005/0015154 | A1 * | 1/2005 | Lindsey ................ A61B 17/68 |
| | | | 623/23.46 |
| 2005/0112397 | A1 * | 5/2005 | Rolfe ................... A61B 17/866 |
| | | | 428/593 |
| 2006/0178749 | A1 | 8/2006 | Pendleton et al. |
| 2010/0100191 | A1 | 4/2010 | May et al. |
| 2010/0268227 | A1 | 10/2010 | Tong et al. |
| 2012/0123553 | A1 | 5/2012 | Sidebotham et al. |
| 2014/0257507 | A1 | 9/2014 | Wang et al. |
| 2015/0018956 | A1 | 1/2015 | Steinmann et al. |
| 2016/0038301 | A1 * | 2/2016 | Wickham ............. A61F 2/4455 |
| | | | 623/17.16 |
| 2016/0106551 | A1 | 4/2016 | Grimberg et al. |
| 2016/0262903 | A1 | 9/2016 | West |
| 2017/0333205 | A1 * | 11/2017 | Joly ..................... A61F 2/4455 |
| 2018/0055643 | A1 * | 3/2018 | Castro .................... A61L 27/58 |
| 2019/0099274 | A1 * | 4/2019 | Duarte ................ A61F 2/30771 |
| 2019/0133783 | A1 * | 5/2019 | Unger ...................... A61F 2/44 |
| 2019/0231554 | A1 * | 8/2019 | Bishop .................. A61F 2/4465 |
| 2019/0343644 | A1 * | 11/2019 | Ryan ................... A61F 2/30771 |
| 2019/0343645 | A1 * | 11/2019 | Miccio ............... A61F 2/30771 |
| 2019/0343652 | A1 * | 11/2019 | Petersheim ........... A61F 2/4455 |
| 2020/0179122 | A1 * | 6/2020 | Stalcup ................. A61F 2/3859 |
| 2020/0261240 | A1 * | 8/2020 | Mesiwala ........... A61F 2/30907 |
| 2020/0289714 | A1 * | 9/2020 | Snell ....................... B29C 43/14 |
| 2021/0000602 | A1 * | 1/2021 | Kumta ................. A61F 2/3094 |
| 2021/0038393 | A1 * | 2/2021 | Yau .......................... A61L 27/00 |

FOREIGN PATENT DOCUMENTS

| | | |
|---|---|---|
| CN | 105722478 A | 6/2016 |
| EP | 2319462 A1 | 5/2011 |
| KR | 10-0279178 B1 | 1/2001 |
| KR | 10-2016-0085506 A | 7/2016 |
| WO | 2013126407 A1 | 9/2013 |
| WO | 2016010701 A1 | 1/2016 |
| WO | 2016044739 A1 | 3/2016 |

OTHER PUBLICATIONS

Mangano, et al. "Direct Metal Laser Sintering Titanium Dental Implants: A Review Of The Current Literature", International Journal of Biomaterials, Dec. 1, 2014.

Ryan, et al., "Fabrication Methods Of Porous Metals For Use In Orthopedic Applications", Biomaterials 27 (2006) 2651-2670, Dec. 7, 2005.

Fogagnolo, et al. "The Effect of the Laser Process Parameters in the Microstructure and Mechanical Properties of T16AL4V Produced by Selective Laser Sintering/Melting", Metal 2012, May 25, 2012.

First Examination Report issued in connection with the corresponding Australian Patent Application No. 2020200666, dated Jun. 30, 2020, 3 pages.

Extended European Search Report issued in connection with the corresponding European Patent Application No. 18793783.4, dated Aug. 10, 2020, 8 pages.

First Office Action issued in connection with the corresponding Chinese Patent Application No. 201880008240.2, dated Sep. 16, 2020, 11 pages.

* cited by examiner

BONE IMPLANT WITH STRUTS

CROSS-REFERENCE TO RELATED APPLICATION

This application is a U.S. national stage application under 35 U.S.C. § 371 of International Application No. PCT/US2018/024458, filed Mar. 27, 2018, which claims benefit under 35 U.S.C. § 119(e) to U.S. Provisional Application Ser. No. 62/501,283, filed May 4, 2017, and entitled "BONE IMPLANT WITH STRUTS," the entireties of which are incorporated herein by reference.

FIELD

This disclosure relates generally to medical devices, and more specifically to implants.

BACKGROUND

A variety of implants have been made by casting or machining the implant from a bar stock of material. In some cases, the implants are provided with a porous or rough structure at the bone-implant interface to promote bone growth into or on the implant. For example, plasma spray can be used on the outside of the implant to provide a roughened surface for bone ingrowth or adhesion. "BIO-FOAM" porous titanium material from Wright Medical Technology® of Memphis, Tenn. is another structure that promotes bone ingrowth.

SUMMARY

In some embodiments, an implant comprises a component for fixed attachment to a bone. An underpass layer of a porous material is disposed on a first side of the component for fixed attachment. At least one strut is provided on the underpass layer. The at least one strut has a first (e.g., distal) surface contacting the underpass layer and a second surface opposite the first surface. The at least one strut comprises a non-porous material. An additional layer of the porous material fills a respective volume adjacent the at least one strut. The additional layer extends from a first side of the underpass layer to a predetermined height equal to or above a height of the second surface of the at least one strut.

In some embodiments, an implant comprises a tibial component shaped to hold a tibial insert having an articulating surface. An underpass layer of a porous material is disposed on a superior side of the tibial component. A plurality of struts are provided on the underpass layer. Each strut has an inferior surface contacting the underpass layer and a superior surface opposite the inferior surface. Each strut comprises a non-porous material. An additional layer of the porous material filling a respective volume between each adjacent pair of struts in the plurality of struts, the additional layer overlying at least a portion of each of the plurality of struts and extending from a superior side of the underpass layer to a predetermined height above the superior surfaces of the struts.

In some embodiments, an implant comprises a component for fixed attachment to a bone. An underpass layer of a porous material is disposed on a first side of the component for fixed attachment. At least one strut is on the underpass layer. The at least one strut has a first surface contacting the underpass layer and a second surface opposite the first surface. The at least one strut comprises a non-porous material, wherein the porous material in the underpass layer is shaped into at least one strip extending perpendicular to a longitudinal direction of the plurality of one or more struts. An additional layer of the porous material fills a respective volume adjacent the at least one strut. The additional layer extends from a first side of the underpass layer to a predetermined height equal to or above a height of the second surface of the at least one strut.

In some embodiments, an implant comprises a fastener having a head and an elongated member. The elongated member has a porous core and a non-porous surface. The porous core comprises a porous material that penetrates the non-porous surface in at least one region.

DETAILED DESCRIPTION

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Some embodiments described herein include an implant having a solid substrate and a porous structure on the bone-contacting surface of the substrate.

Figure 1:
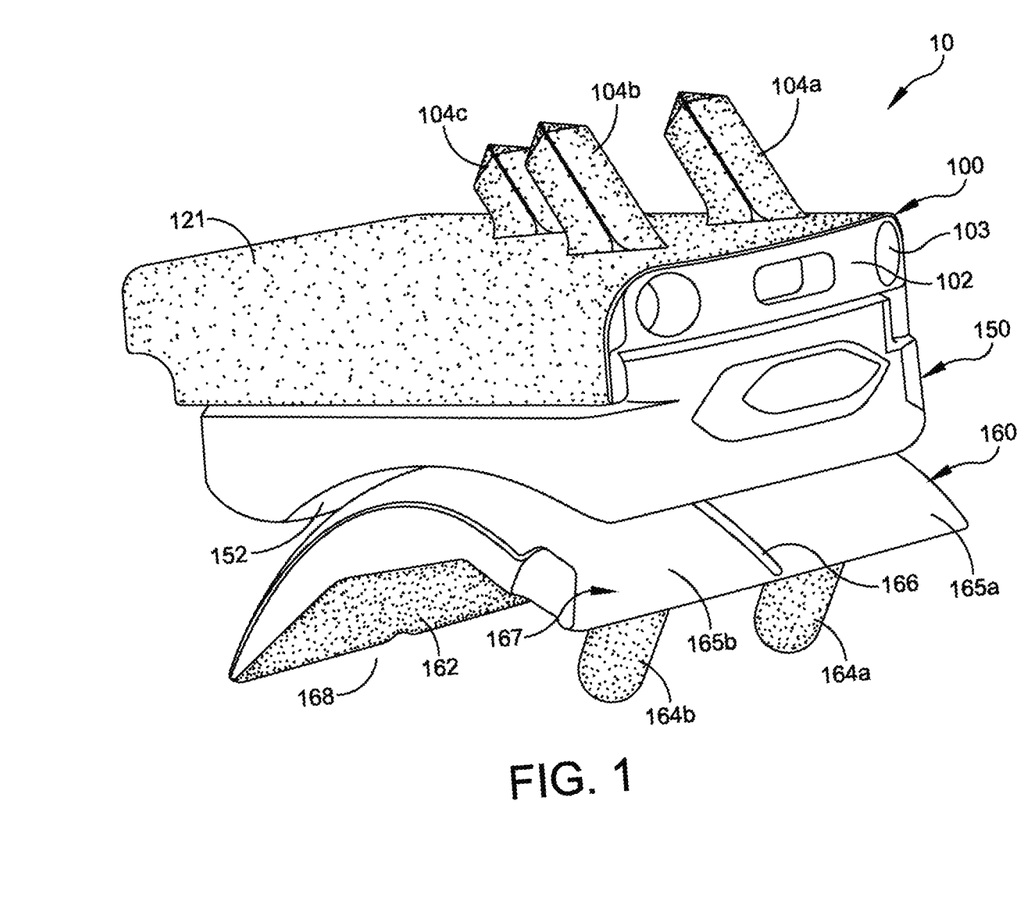
FIG. 1 is an isometric view of an implant according to some embodiments.

FIG. 1 is an isometric view of an implant 10 according to some embodiments. In some embodiments, the implant 10 is a total ankle replacement prosthesis. The implant 10 includes a component for fixed attachment to a first bone (e.g., a tibia) and a component for fixed attachment to a second bone (e.g., a talus). In FIG. 1, the component for fixed attachment to the first bone is a tibial tray 100. The tibial tray 100 has a substrate 102 with a porous bone-interfacing surface 121 having three pegs 104a-104c projecting therefrom. The tibial tray 100 is configured to hold a removable tibial insert comprising polyethylene ("poly insert") 150 having an articulating surface 152. In some embodiments, as shown in FIG. 1, the pegs 104a-104c have a square cross-section. In other embodiments, the pegs have a round cross-section.

In FIG. 1, the component for fixed attachment to the second bone is a talar dome 160 having an articulating surface 167, comprising two convex curved lobes 165a, 165b with a sulcus or groove 166 therebetween. The talar dome 160 has a porous bone-facing surface 162. In some embodiments, as shown in FIG. 1, the talar dome 160 has a chamfered cut (or cuts) 168 for implanting on a chamfered resected talus. The chamfered cut(s) 168 provides resistance to relative rotation between the talus and the talar dome 160. The talar dome 160 has a plurality of pegs 164a, 164b for fixing the talar dome to the talus. In other embodiments, the components for fixed attachment can include, but are not limited to, total knee replacement components, hip replacement components, shoulder replacement components, bone screws, or the like.

The implants described herein can be made by direct metal laser sintering (DMLS). DMLS is an additive manufacturing (AM) process by which products can be printed using a laser or e-beam joining sequential layers of powder metal (e.g., Ti6Al4V or CoCr or Stainless Steel, for example) under automated computer control. Highly porous structures are good candidates for AM. Highly porous structures also provide good bone in-growth properties.

Figure 2A:
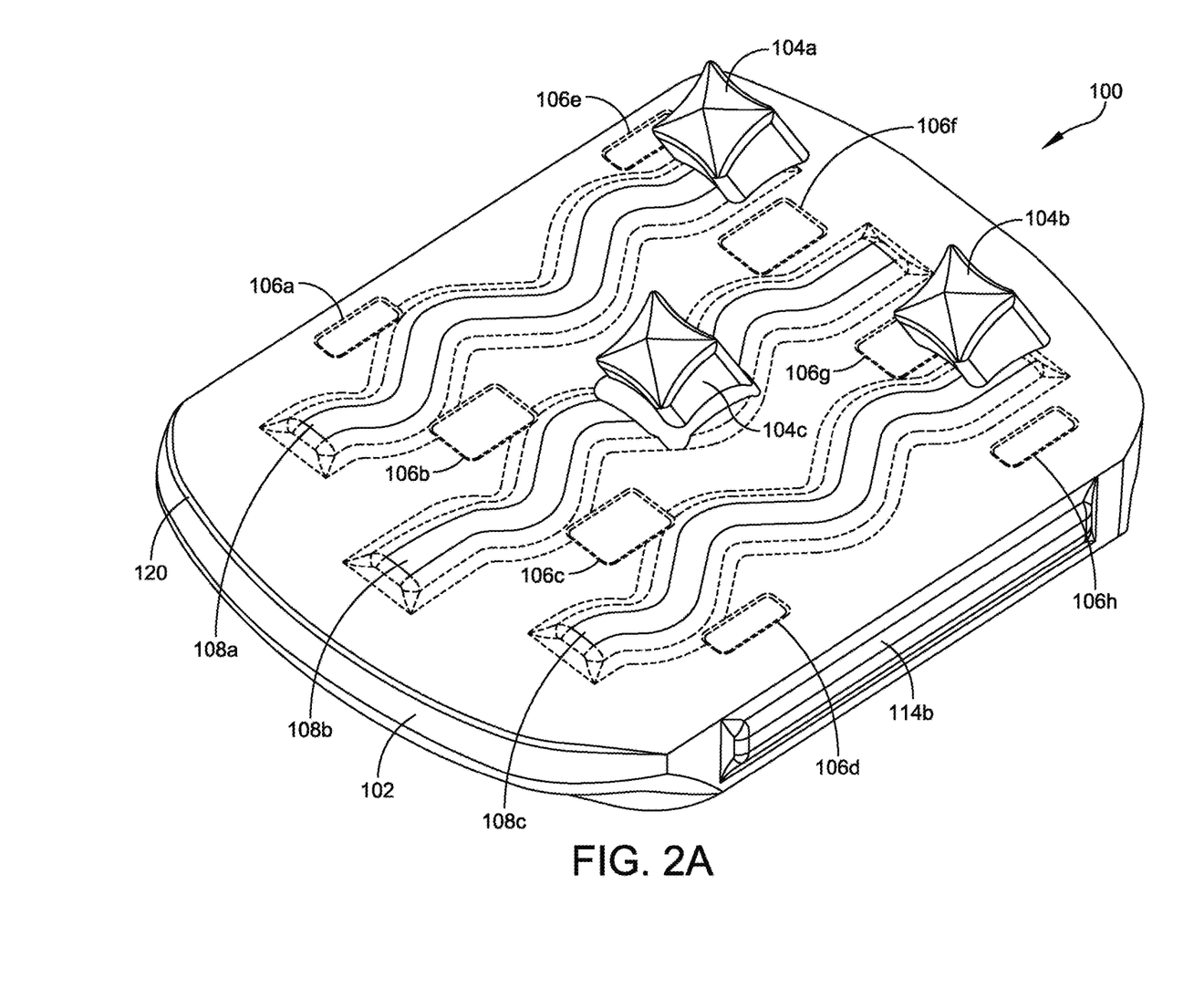
FIG. 2A is an isometric superior view of the solid portion of the tibial tray of FIG. 1.
Figure 2B:
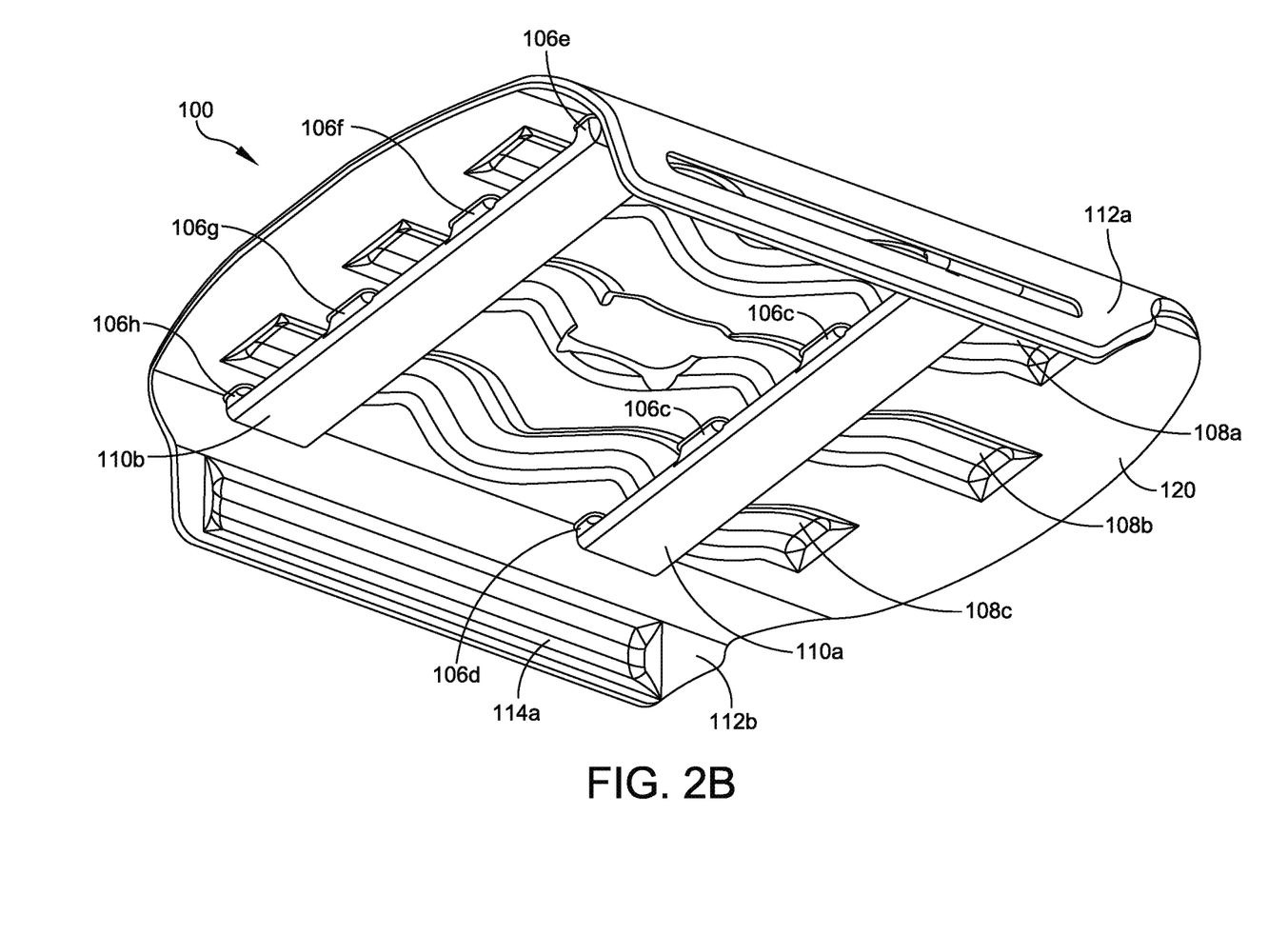
FIG. 2B is an isometric inferior view of the porous portion of the tibial tray of FIG. 1.

Reference is now made to FIGS. 2A and 2B. Additive manufactured (AM) solid components are potentially not as strong as solid components having the same material, size and shape, but cast, forged, cold worked, or machined from bar stock. To increase the strength of the tibial tray 100, stiffening solid struts 108a-108c (FIG. 2A, 2B) can be added. The struts 108a-108c are at least partially embedded in, or protrude into, the porous structure 120.

The present inventors have added struts of solid material 108a-108c within a porous material layer, as shown in FIGS. 2A and 2B. The solid material of the substrate 102 is stronger than the porous material 120. Nevertheless, if solid, non-porous areas of an implant are in direct contact with bone, there is a chance of an osteolytic pathway forming, leading to loss of bone tissue.

The underpass(es) can connect (otherwise unconnected) regions having non-porous structures (e.g., struts or other non-porous solid structures) therebetween. For example, as best seen in FIG. 2B, the underpasses 110a, 110b can be perpendicular to the struts of solid material 108a-108c and can extend beneath the struts of solid material 108a-108c. In some embodiments, to make sure bone grows all around the bone-interfacing surface 121, the tibial tray 100 can have porous material or a roughened surface covering the entire bone-interfacing surface 121. Using an AM process ensures that there is no gap in the structure of the tibial tray 100, as an additive manufacturing process can print porous regions abutting non-porous regions in any desired configuration, including non-porous regions embedded inside porous regions, and/or including porous regions embedded inside non-porous regions.

In other embodiments, to make sure bone grows all around the bone-interfacing surface 121, the entire bone-interfacing surface 121 the tibial tray 100 has a textured or rough surface. An AM process can form a rough surface on or in a thin layer of material.

Figure 2C:
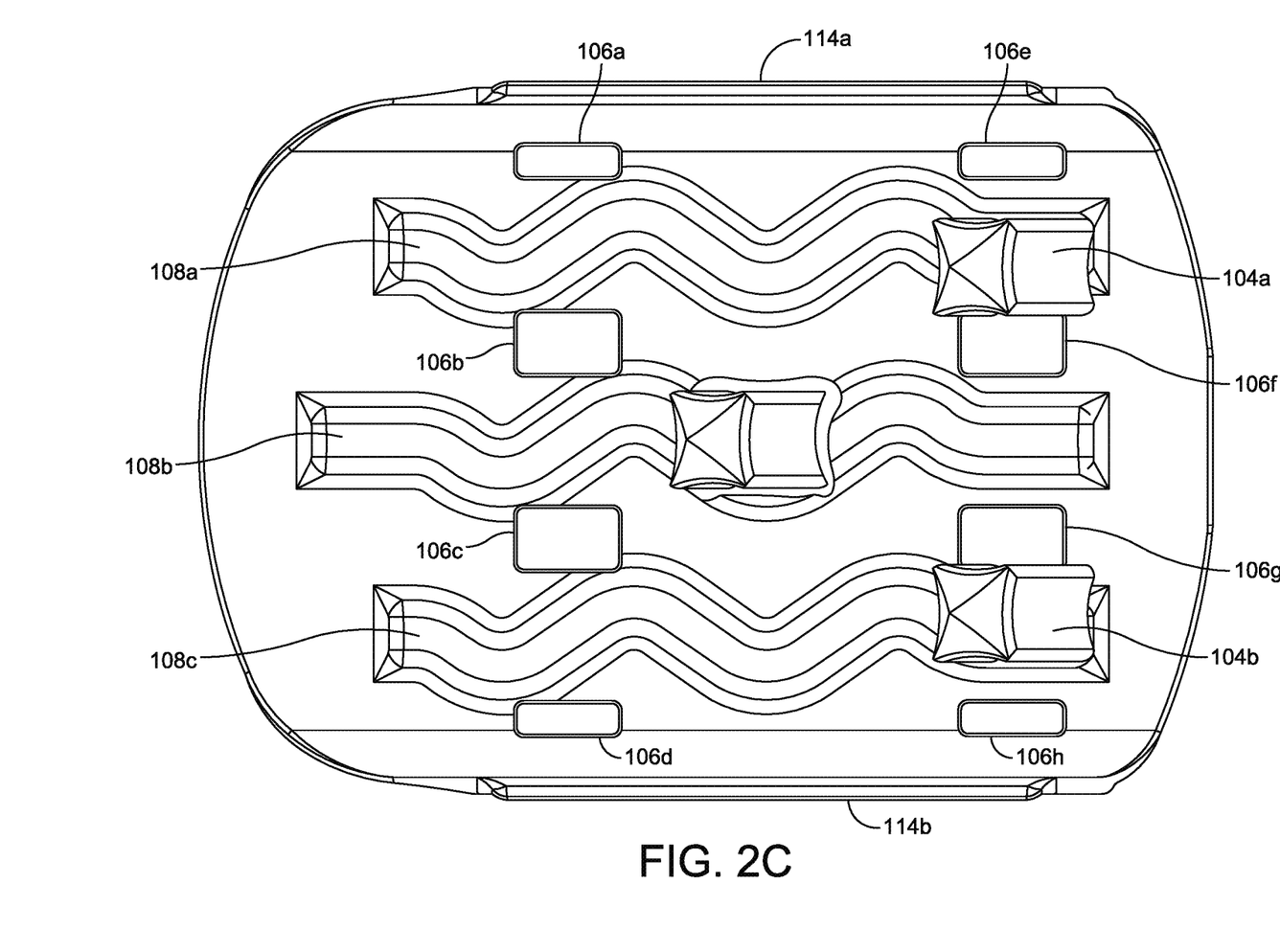
FIG. 2C is a top superior view of the solid portion of the tibial tray of FIG. 1.

FIG. 2C is a superior view of the solid portion of the tibial tray 100 showing the struts 108a-108c. FIG. 2C schematically shows openings for connecting portions 106a-106h of the porous material between the porous material in the underpass layers 110a, 110b and the porous material 120 at the surface 121 of the tibial tray. Although FIG. 2C shows the connecting portions 106a-106h shaped as distinct rectangular pillars, the connecting portions are continuous with the porous material on the anterior and posterior sides of the connecting portions, and extend medially and laterally the entire distance between adjacent struts 108a-108c. FIG. 2C also shows ribs 114a, 114b projecting from the medial and lateral edges of the tibial tray. The ribs 114a, 114b provide additional strength adjacent to the trapezoidal opening 105 (FIG. 4) in the inferior side of the tibial tray 100. The trapezoidal opening 105 forms a "dovetail" joint with the poly insert 150 (FIG. 1). In some embodiments, a locking mechanism is provided to retain the poly insert 150 in the tibial tray 100. For example, the locking mechanism can include a pair of fasteners (e.g., screws) that lock the poly insert 150 in place.

Figure 3:
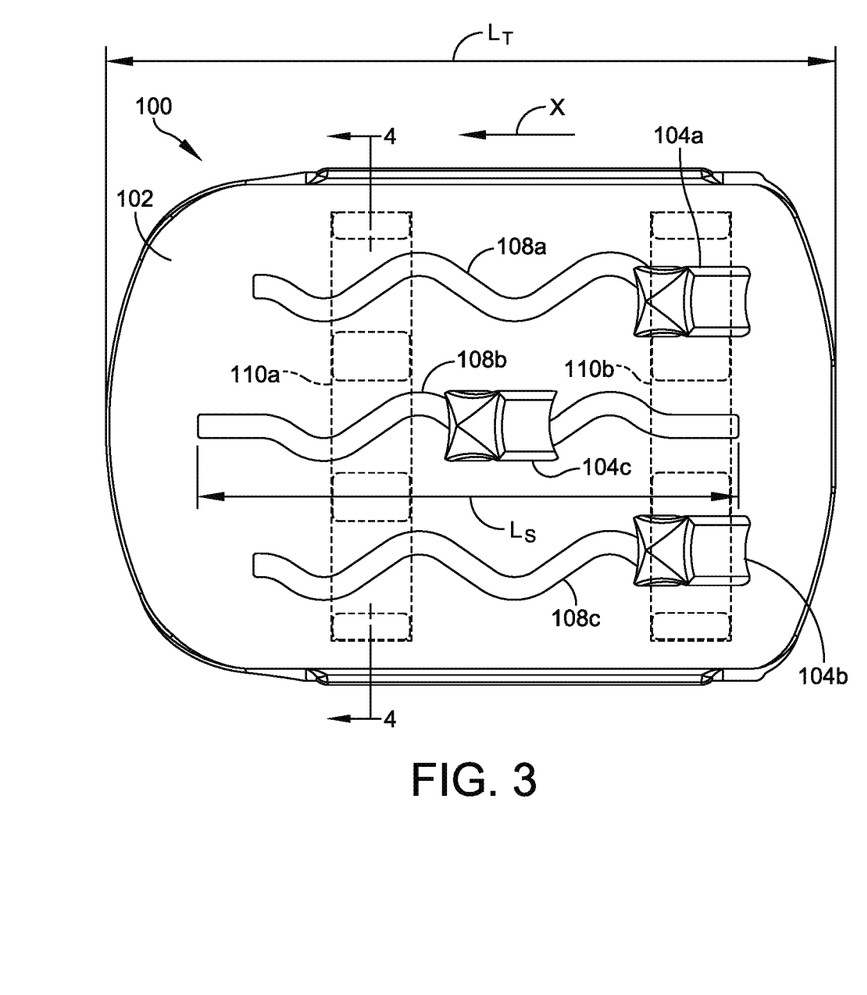
FIG. 3 schematically shows the struts and underpasses of the tibial tray of FIG. 1.

FIG. 3 is a plan view of the tibial tray 100 of FIG. 1, showing the relative locations of the struts 108a-108c and "porous underpasses" 110a, 110b. In some embodiments, as shown in FIG. 3, porous underpasses 110a, 110b are added beneath the struts 108a-108c, allowing bone to grow across the porous underpasses 110a,110b, and beneath the struts 108a-108c. In some embodiments, the porous material in the underpass layer 110a is shaped into at least one strip extending perpendicular or non-parallel to a longitudinal direction X of the plurality of struts 108a-108c. In some embodiments, both the underpasses 110a, 110b can be strips of porous material oriented perpendicular to the struts 108a-108c, in a layer adjacent to the layer of the struts. These underpasses 110a, 110b are connected to, and continuous with, the porous structure 120 on the substrate to allow bone to grow across the struts 108a-108c, in the adjacent layer beneath the struts. Some embodiments comprise multiple underpasses 110a, 110b within a single tibial tray 100 (or other implant component). Some embodiments comprise multiple (e.g., two, three, four, and more than four) underpasses 110a, 110b abutting a single strut 108a. In some embodiments, one of the underpasses 110a, 110b abuts all of the struts 108a-108c. In some embodiments, as shown in FIG. 3, each individual underpass 110a, 110b crosses all of the struts 108a-108c. In some embodiments, the underpasses 110a, 110b cover a relatively small portion of the area of the tibial tray 100. For example, the underpasses may cover from about 10% to about 50% of the bottom surface area of the tibial tray 100. In some embodiments, the underpasses may cover from about 20% to about 40% of the area of the tibial tray 100. In some embodiments, the underpasses may cover from about 25% to about 35% of the area of the tibial tray 100. Some embodiments have a large continuous underpass through the majority of the tibial tray 100.

When growing bone tissue reaches a solid barrier, the bone can cross over gaps on the order of microns. The present inventors have determined that porous underpasses 110a, 110b can provide a bone growth path across wider structures (on the order of millimeters) such as solid struts. In more detail, in some embodiments, the width of the struts 108a-108c is on the order of 200 microns (3 mm). The porous underpasses can provide a connection between two porous regions separated by a non-porous region. The porous underpass material crosses underneath the non-porous region." The strut and underpass combination can be included in a variety of implants, such as, but not limited to, a tibial tray, a talar plate, a bone screw, total knee replacement components, hip replacement components, shoulder replacement components, or the like.

FIGS. 4-8 show additional details of the exemplary tibial tray 100. The tibial tray 100 includes a component 100 for fixed attachment to a bone (not shown). An underpass layer 110a, 110b (FIGS. 2, 3) of a porous material is disposed on a first (e.g., proximal) side of the component 100 for fixed attachment. At least one strut 108a is provided adjacent? the underpass layer 110a, 110b. Some embodiments have a plurality of struts 108a-108c. The at least one strut 108a-108c has a second surface 122a-122c contacting the underpass layer 110a, 110b and a first (e.g., proximal) surface opposite the second surface. The at least one strut 108a-108c includes a non-porous material. An additional layer 120 of the porous material fills a respective volume adjacent the at least one strut 108a-108c. The additional layer 120 fills the region between adjacent struts 108a-108c, up to the height of a top surface of the struts. In some embodiments, the height of the additional layer is equal to the height of the struts, and the additional layer has a rough top surface.

In some embodiments, the material of the porous layer extends to a height above the top surface and overlies at least a portion of the at least one strut 108a. In some embodiments, the additional layer extends from a first side of the underpass layer 110a, 110b to a predetermined height above the first surface of the at least one strut 108a, forming a layer of the porous material having a thickness Ts (shown in FIG. 5A) covering the strut. In some embodiments, the superior surface 121 of the additional layer 120 covers the entire superior side of the tibial component. In other embodiments, the additional layer 120 does not cover strut (Ts not present). Still, the additional layer is continuous by passing under strut as porous underpass.

FIGS. 4-8 show additional views of the implant 100 of FIGS. 2A-3. The implant 100 includes a tibial component 100 shaped to hold a poly insert 150 (FIG. 1) having an articulating surface. The tibial component 100 has a substrate 102 of a non-porous material. An underpass layer 110a, 110b of a porous material is disposed on a superior side of the tibial component 100. A plurality of struts 108a-108c are provided on the underpass layer 110a, 110b. Each strut 108a-108c has an inferior surface 122a-122c contacting the underpass layer 110a, 110b and a superior surface 123a-123c opposite the inferior surface 122a-122c. Each strut 108a-108c comprises a non-porous material.

An additional layer 120 of the porous material fills a respective volume between each adjacent pair of struts 108a-108c in the plurality of struts. The additional layer 120 overlies at least a portion of each of the plurality of struts 108a-108c and extends from a superior side of the underpass layer 110a, 110b to a predetermined height above the superior surface 123a-123c of the struts, forming a layer of the porous material having a thickness Ts (shown in FIG. 5A) covering the struts.

In some embodiments, the porous material 120 and the non-porous material of the substrate 120 have the same composition as each other, but a different average density from each other. For example, both the non-porous and porous material can be titanium, Ti6Al4V, CoCr, Stainless Steel, a polymer, such as Polyether ether ketone (PEEK), a ceramic such as pyrocarbon, and combinations thereof. The non-porous material is a continuous bulk solid without voids. In other embodiments, the porous layer 120 or a portion of the porous layer (e.g., underpasses 110a, 110b) can comprise a different composition from the composition of the non-porous material. For example, in some embodiments, the underpasses 108a-108c comprise a resorbable material (e.g., polymer or absorbable metals), but the rest of the porous and non-porous material in the talar tray 100 comprises a permanent implant material, such as Ti6Al4V, CoCr, Stainless Steel, or PEEK.

The porous material is in the form of a mesh, matrix or web with interconnected voids and interstices. The porous material can have the appearance of an open-celled foam (even though it is formed by a DMLS process).

The struts 108a-108c can have a variety of configurations. In some embodiments (not shown), the struts extend across the entire length $L_T$ of the tibial tray 100. In other embodiments, as shown in FIG. 3, the struts 108a-108c have a length Ls shorter than the entire length $L_T$ of the tibial tray 100. The short length Ls of the struts 108a-108c can leave a porous region adjacent each end of the struts, which may promote bone growth, and close off an osteolysis pathway of the solid substrate at the ends of the struts. As shown in FIGS. 1 and 3, the tibial component 100 has a length $L_T$—the same length as the implant 10—and each of the plurality of struts 108a-108c has a respective length Ls less than the length $L_T$ of the tibial tray 100.

In some embodiments (FIG. 10), the struts 158a-158c are elongated line segments. In other embodiments, the struts 108a-108c (FIGS. 1, 3, 10) have an undulating (sine-wave shaped) configuration to help compensate for off-center loading, which may induce a twisting and bending moment. In other embodiments (not shown), the struts have other periodic shapes, such as saw-tooth, triangular, square wave, curved (with a single radius), or the like.

Figure 4:
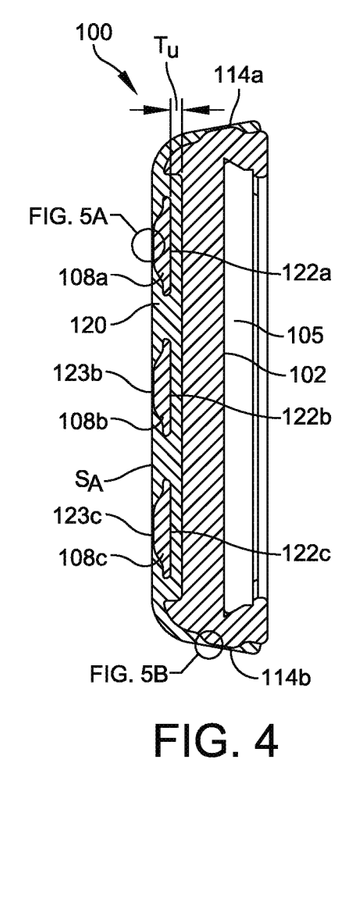
FIG. 4 is a cross-sectional view of the tibial tray of FIG. 3, taken across section line 4-4.

In some embodiments, as best seen in FIG. 4, the plurality of struts 108a-108c have a cross-section that is wider at the inferior surface 122a-122c of each strut than at the superior surface 123a-123c of each strut. In other embodiments (not shown), the plurality of struts 108a-108c have a cross-section that is narrower at the inferior surface of each strut than at the superior surface of each strut. In some embodiments, the cross-section can have a trapezoidal shape. As shown in FIG. 4, the non-horizontal sides of the trapezoidal shape can be slightly concave. In other embodiments (not shown), the non-horizontal sides are straight diagonal lines. In other embodiments (not shown), the struts have a rectangular cross-section. The solid struts may be provided in alternative shapes and surface areas depending on the implant type. For example, an implant which is subject to higher loads and stresses may have struts shaped and numbered to withstand higher loads.

In some embodiments, the tibial tray 100 further comprises at least one peg 104a-104c extending in a superior direction from a respective one of the plurality of struts 108a-108c. The example in FIGS. 1-8 includes three pegs 108a-108c, but other embodiments can have any desired number of pegs. In some embodiments, the pegs 104a-104c have a non-porous interior and a porous exterior surface. In other embodiments, the entire pegs (including the surface) is made of the non-porous material. In other embodiments (not shown), the pegs have a porous region at the interface between the peg and the tibial tray, and the remainder of each peg is formed of porous material.

Figure 5A:
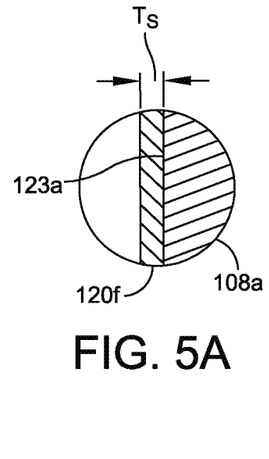
FIGS. 5A and 5B are enlarged details of FIG. 4.
Figure 5B:
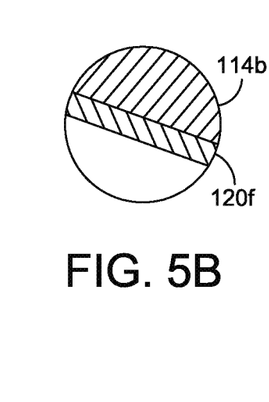

In some embodiment, as best seen in FIG. 4, the additional layer 120 of porous material extends from the superior surface 122a-122c of the underpass layer 110a, 110b slightly past the superior surface 123a-123c of the struts 108a-108c. As shown in FIG. 5A, a thin layer 120f of the porous material may optionally cover the superior surfaces 123a-123c of the struts 108a-108c, so the superior surface SA of the additional layer 120 covers the entire superior side of the tibial tray 100, providing a continuous porous layer constituting the bone-contacting surface of the tibial tray 100. In some embodiments, the thickness Tu (FIG. 4) of the underpass layer 110a, 110b is greater than a thickness Ts (FIG. 5A) between the superior surface 123a-123c of each of the plurality of struts and a superior surface of the additional layer 120.

In some embodiments, the thickness Ts of the porous material adjacent to the struts 108a-108c is about 0.75 mm (0.030 inch) thick. In some embodiments, the tibial tray is pressed into the bone, so about 0.020 inch of the porous material embeds in the bone, and a small layer (e.g., 0.005 inch) of the porous material separates the bone and the superior surface of the struts 108a-108c. Throughout the procedure, the struts 108a-108c remain separated from the bone, below the surface of the porous material. This promotes bone growth at the bone-implant interface. In other embodiments, the top surface of the porous material has a height above height of the struts, but the porous surface does not cover the struts; the porous material touches the bone first even if no porous material covers the struts.

Figure 6:
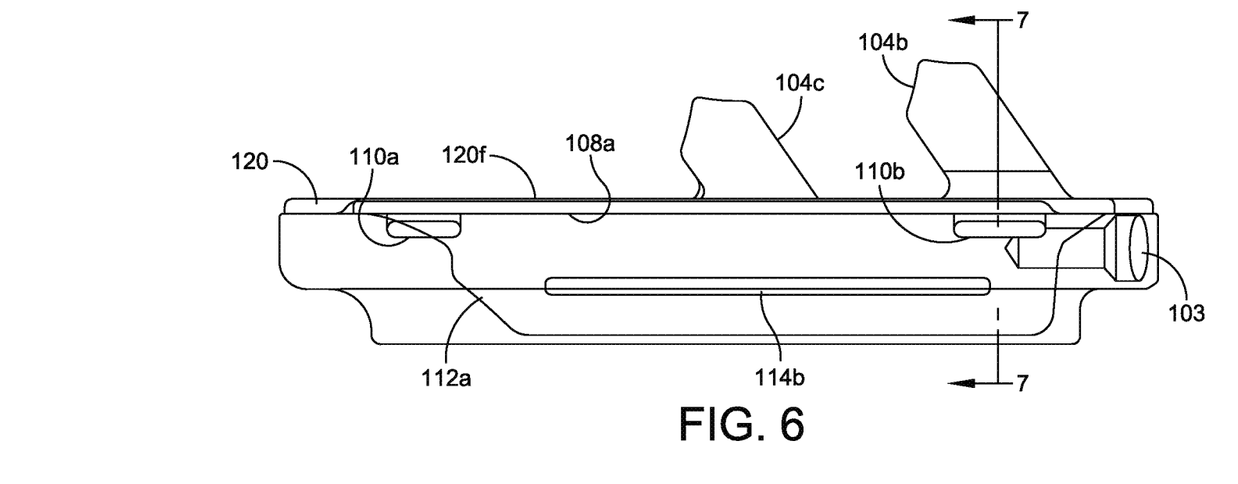
FIG. 6 is a medial view of the tibial tray of FIG. 1.

FIG. 6 is a side view of an embodiment of the tibial tray 100. The tibial tray 100 has two holes 103. When the poly insert 150 is inserted in the tibial tray 100, screws are inserted through the holes 103 for firmly attaching the poly insert 150. This is the exposed side strut as seen in solid portion in FIG. 7.

Figure 7:
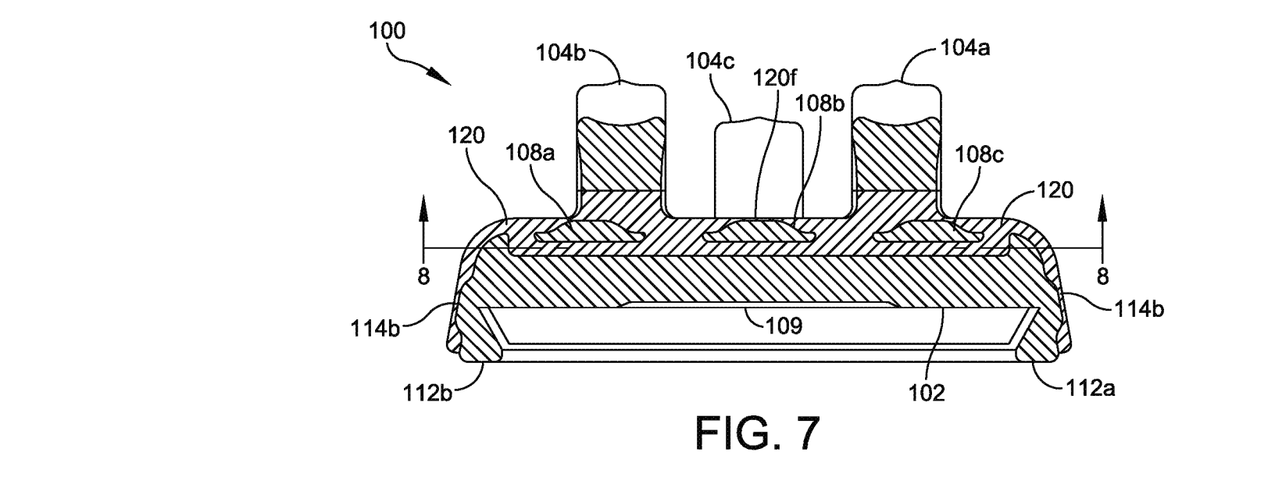
FIG. 7 is a cross-sectional view of the tibial tray of FIG. 6, taken across section line 7-7.

FIG. 7 is a cross-sectional view taken across section line 7-7 of FIG. 6. In FIGS. 4 and 7, like reference numerals indicate like structures. FIG. 7 shows the cross-sections of pegs 104a and 104b. In some embodiments, the porous material 120 can extend part way up the length of the pegs as shown. FIG. 7 also shows a channel 109 for accommodating a corresponding feature of a poly insert (not shown). In other embodiments, the shape of the inferior surface of the tibial tray 100 can be varied, corresponding to different means of attaching the poly insert and/or different configurations of the poly insert.

Figure 8:
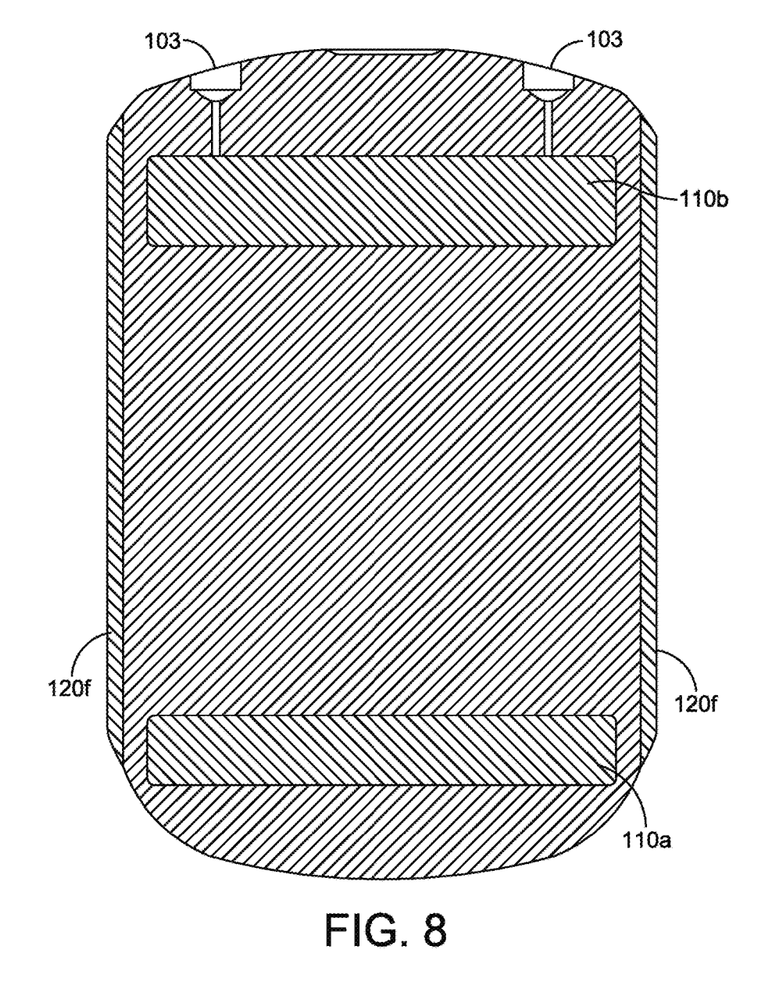
FIG. 8 is a cross-sectional view of the tibial tray of FIG. 7, taken across section line 8-8.

FIG. 8 is a cross-sectional view taken across section line 8-8 of FIG. 7. FIG. 8 shows the porous material of the underpass layers 110a, 110b and the medial and lateral edges 120f formed in the same continuous layer as the non-porous material of the substrate 102.

Figure 9:
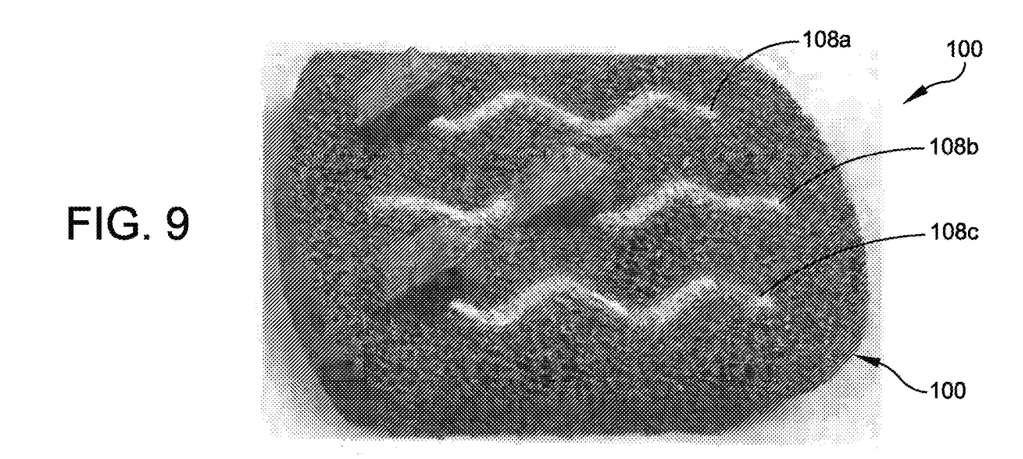
FIGS. 9 and 10 are photographs of two examples fabricated according to this disclosure.

FIG. 9 is a photograph of a tibial tray 100 as described above with respect to FIGS. 1-8. In some embodiments, the solid struts 108a-108c are visible beneath the thin layer 120 of porous material at the surface SA (FIG. 4) of the tibial tray 100. In the example of FIG. 9, the center strut 108b is longer than the medial and lateral struts 108a, 108c. In other embodiments, all of the struts 108a-108c have the same length. In some embodiments, one or more of the struts 108a-108c extend from the anterior end of the tibial tray 100 to the posterior end. In other embodiments, there are fewer than, or more than, three struts.

Figure 10:
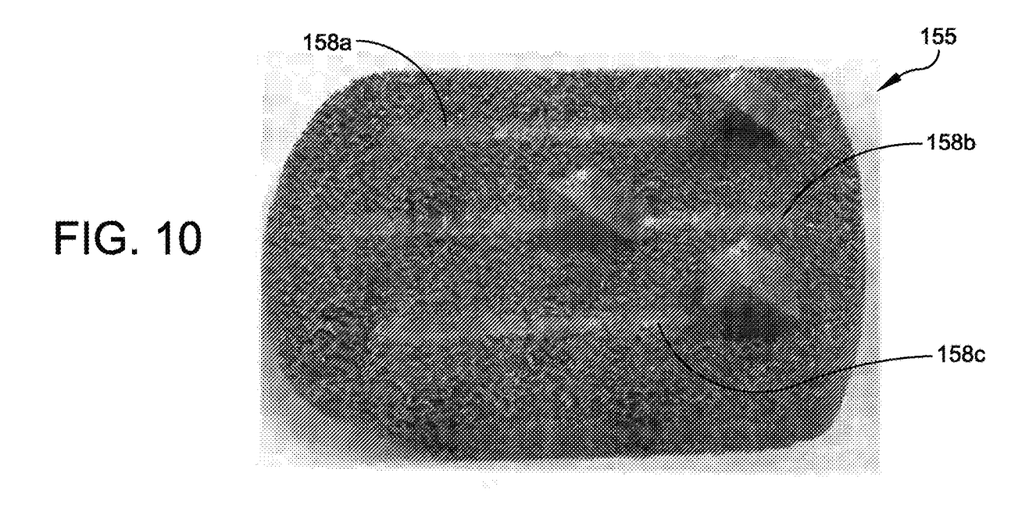

FIG. 10 is a photograph of an embodiment of a tibial tray 155. In some embodiments, as shown in FIG. 10, the solid struts 158a-158c are straight line segments beneath the thin layer 120 of porous material at the surface SA (FIG. 4) of the tibial tray 155. In the example of FIG. 10, the center strut 158b is longer than the medial and lateral struts 158a, 158c. In other embodiments, all of the struts 158a-158c have the same length. In some embodiments, one or more of the struts 158a-158c extend from the anterior end of the tibial tray 155 to the posterior end. In other embodiments, there are fewer than, or more than, three struts.

In some embodiments, the underpass layer 110a, 110b comprises a resorbable material such as a magnesium alloy, which may contain lithium, aluminum, rare earth metals (e.g., neodymium or cerium), manganese, zinc or other metals. In other embodiments, the resorbable material can include, but are not limited to polymer materials including a polylactide, polyglycolide, polycaprolactone, polyvalerolactone, polycarbonates, polyhydroxy butyrates, poly ortho esters, polyurethanes, polyanhydrides, and combinations thereof, for example.

In some embodiments, the underpass layer comprises a biologic material, such as a coating containing osteoinductive or osteoconductive biological components. The biologic material can include bone morphogenetic factors, i.e., growth factors whose activity are specific to bone tissue including, but not limited to, demineralized bone matrix (DBM), bone protein (BP), bone morphogenetic protein (BMP), and mixtures and combinations thereof. Additionally, formulations for promoting the attachment of endogenous bone may comprise bone marrow aspirate, bone marrow concentrate, and mixtures and combinations thereof.

Although FIG. 1 shows a chamfered talar dome 160, in other embodiments (not shown), the talar dome has a curved or flat bone interfacing surface.

Although FIG. 1 shows a unitary talar dome 160, in other embodiments (not shown), the talar component of the implant 10 comprises a permanently implanted talar plate (with or without an augment) interfacing to the bone, and a removable talar dome attachable to the talar plate, where the talar dome has an articulating surface.

This disclosure is not limited to tibial ankle implants. Other types of implants can include struts and underpasses.

Figure 11A:
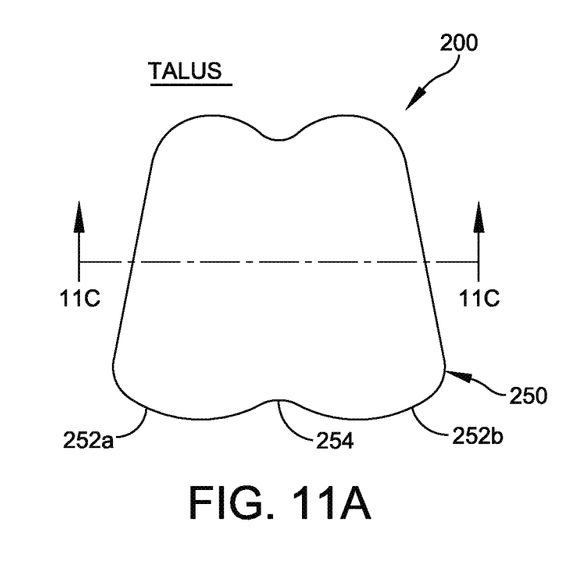
FIG. 11A is a superior view of a talar implant according to another embodiment.
Figure 11B:
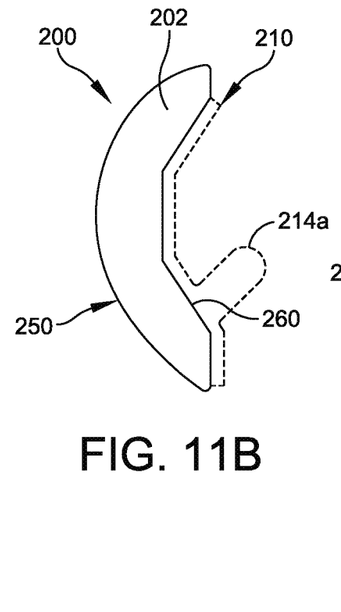
FIG. 11B is a medial side view of the talar implant of FIG. 11A.
Figure 11C:
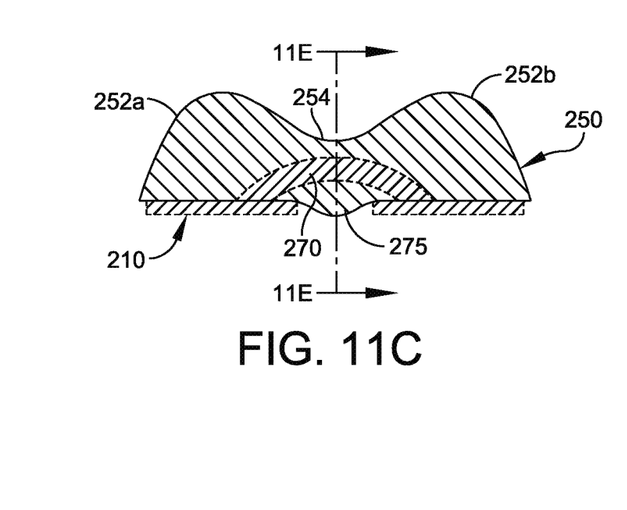
FIG. 11C is a cross-sectional view taken along section line 11C-11C of FIG. 11A.
Figure 11D:
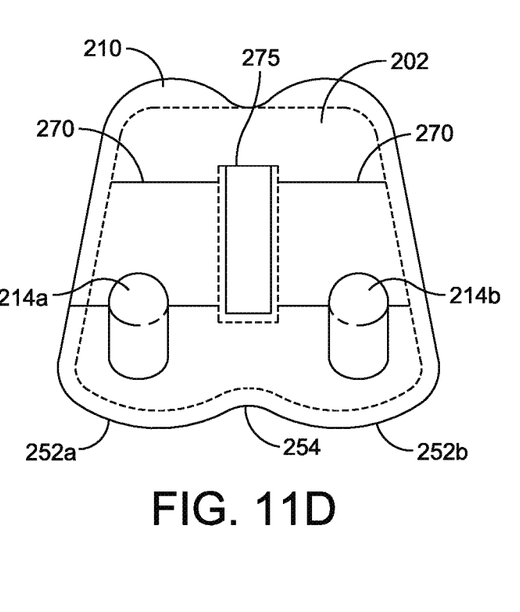
FIG. 11D is an inferior view of the talar implant of FIG. 11A.
Figure 11E:
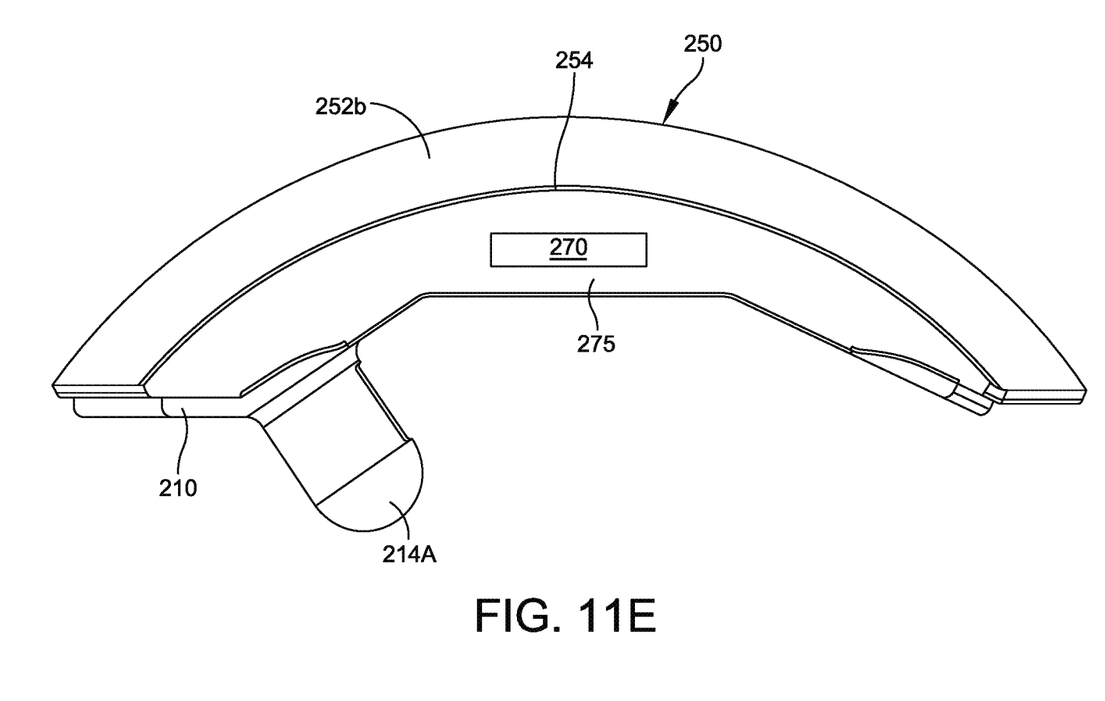
FIG. 11E is a cross-sectional view taken along section line 11E-11E of FIG. 11C.

For example, FIGS. 11A-11D show an embodiment of a talar implant 200. FIG. 11A is a superior view of the talar implant 200, and FIG. 11D is an inferior view of the talar implant 200. FIG. 11C is a cross-sectional view taken along section line 11C-11C of FIG. 11A. FIG. 11B is a medial side view of the talar implant 200. In some embodiments, the talar implant 200 is a unitary device with a non-porous talar dome 250 and a porous layer 210 on the bone-facing (inferior) side of the implant 200. The talar dome 250 has an articulating surface including two convex, generally ovoid portions 252a, 252b with a sulcus 254 (FIG. 11C) therebetween. The implant 200 is configured with a chamfered inferior surface 260 for fixed attachment to a chamfered bone. The porous layer 210 includes an underpass layer 270 of the porous material disposed on the inferior surface 260 of the substrate 202.

The implant 200 has at least one strut 275, with a superior side of the strut 275 on the inferior side of the underpass layer 270. The strut 275 is located adjacent to the sulcus 254. The at least one strut comprises a non-porous solid material. The at least one strut 275 has a superior (distal) surface contacting the underpass layer 270 and an inferior (proximal) surface opposite the second surface. In some embodiments, the porous material layer 210 extends in the inferior direction to cover the strut 275 with a thin layer of the porous material. The porous material above the superior surface 123a-123c of the struts has a thickness Ts as discussed above with reference to FIG. 5A.

An additional layer 210 of the porous material fills a volume adjacent the at least one strut 275. In some embodiments, the additional layer 210 overlies at least a portion of the at least one strut 275 and extends from a first (e.g., proximal) side of the underpass layer 270 to a predetermined distance Ts above the first (e.g., proximal) surface of the at least one strut.

The talar implant 200 can comprise any of the materials discussed above for use in the tibial tray 100.

In some embodiments suitable for implantation on a flat resected talus, the implant can have a flat inferior surface for interfacing with the talus. In other embodiments, the implant 200 includes a separate component for fixation to bone (e.g., a talar plate 210), which can be flat (not shown) or chamfered. The talar plate 210 has a non-porous substrate 202 and a porous layer 256 on the inferior (bone-facing) side of the talar plate.

This disclosure is not limited to ankle prostheses. Struts and porous underpasses can be included in other implants, such as—but not limited to—ankle replacements, intramedullary nails, knee replacements, shoulder replacements, hip replacements, elbow replacements, or bone screws.

Figure 12A:
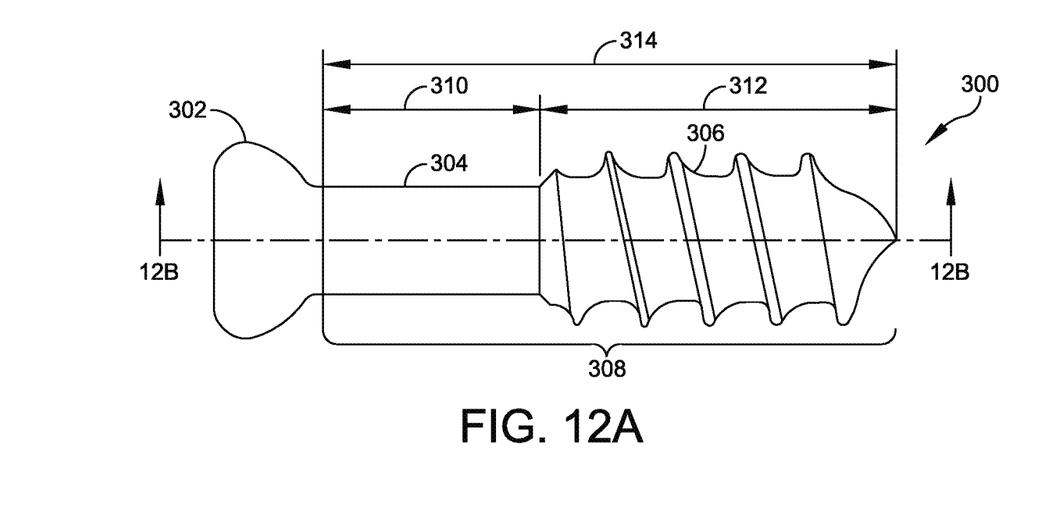
FIG. 12A is a side view of a bone screw according to some embodiments.
Figure 12B:
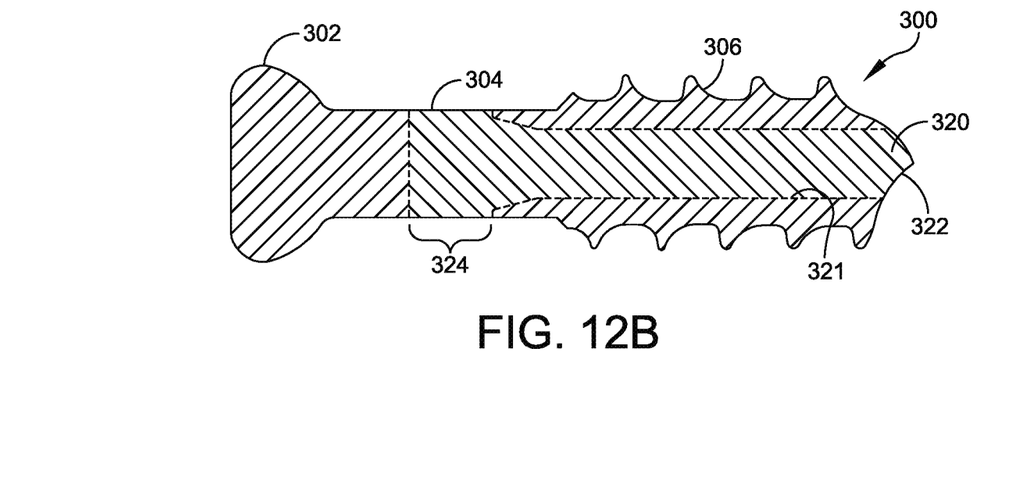
FIG. 12B is a cross-sectional view of the bone screw of FIG. 12A, taken across section line 12B-12B.

FIGS. 12A and 12B show a fastener 300 having porous and non-porous portions. The fastener 300 includes a head 302 and an elongated member 308. The elongated member 308 has a threaded second portion 306 opposite the head 302 and a non-threaded first (e.g., proximal) portion 304 adjacent the head 302. The elongated member 308 has a porous core 320 and a non-porous shell 321. The porous core constitutes an underpass region for the circumferential non-porous shell 321. The porous core 320 comprises a porous material that penetrates the non-porous shell 321 in at least one region 322, 324. In some embodiments, the at least one region includes a first region 322 at a second end of the second portion 306 opposite the head 302, and a second region 324 on a side of the first portion 304. In some embodiments, the second region 324 is located on a circumferential surface of the non-threaded first portion 304 of the fastener 300. In other embodiments, at least one underpass region may be intermittently disposed along a length of the screw, penetrating from a medial to a lateral portion of the screw, along a length thereof. The underpass regions may be disposed between at least one screw pitch or thread The elongated member 308 has a length 314, which equals a sum of the length 310 of the first portion 304 plus the length 312 of the second portion 306. In some embodiments, the length 312 of the second portion 306 is greater than the length 310 of the first portion 304.

The fastener 300 can comprise any of the materials discussed above for use in the tibial tray 100.

Although the subject matter has been described in terms of exemplary embodiments, it is not limited thereto. Rather, the appended claims should be construed broadly, to include other variants and embodiments, which may be made by those skilled in the art.

What is claimed is:

1. An implant comprising:
a component for fixed attachment to a bone;
an underpass layer of a porous material disposed on a first side of the component for fixed attachment;
at least one strut on the underpass layer, the at least one strut having a first surface contacting the underpass layer and a second surface opposite the first surface, the at least one strut comprising a non-porous material; and
an additional layer of the porous material filling a respective volume adjacent the at least one strut, the additional layer extending from a first side of the underpass layer to a predetermined height equal to or above a height of the second surface of the at least one strut.

2. The implant of claim 1, wherein:
the component for fixed attachment is a tibial tray,
the implant further comprises a tibial insert having an articulating surface.

3. The implant of claim 1, wherein:
the component for fixed attachment is a talar plate, and
the implant further comprises a removable talar dome having an articulating surface.

4. The implant of claim 3, wherein the talar dome has a sulcus, and the at least one strut is located adjacent to the sulcus.

5. An implant comprising:
a tibial ankle component shaped to hold a tibial insert having an articulating surface;
an underpass layer of a porous material disposed on a superior side of the tibial component;
one or more struts on the underpass layer, each of the one or more struts having an inferior surface contacting the underpass layer and a superior surface opposite the inferior surface, each of the one or more struts comprising a non-porous material; and
an additional layer of the porous material filling a respective volume between each adjacent pair of struts in the one or more struts, the additional layer extending from a superior side of the underpass layer to a predetermined height at or above the superior surfaces of the one or more struts.

6. The implant of claim 5, wherein the porous material and the non-porous material have a same composition.

7. The implant of claim 5, wherein the tibial component has a length and each of the plurality of struts has a respective length less than the length of the tibial component.

8. The implant of claim 5, further comprising at least one peg extending in a superior direction from a respective one of the plurality of struts, the peg having a non-porous interior and a porous exterior surface.

9. The implant of claim 5, wherein the plurality of struts have an undulating configuration.

10. The implant of claim 5, wherein the plurality of struts have a cross-section that is wider at the inferior surface of each strut than at the superior surface of each strut.

11. The implant of claim 5, wherein a thickness of the underpass layer is greater than a distance between the superior surface of each of the one or more struts and a superior surface of the additional layer.

12. The implant of claim 5, wherein the superior surface of the additional layer covers the entire superior side of the tibial component.

13. The implant of claim 5, wherein the porous material in the underpass layer is shaped into at least one strip extending perpendicular to a longitudinal direction of the one or more struts.

14. The implant of claim 5, wherein the at least one strip extends beneath all of the one or more struts.

15. The implant of claim 5, wherein the underpass layer comprises a resorbable material.

16. The implant of claim 5, wherein the underpass layer comprises a biologic material.

17. An implant comprising:
a component for fixed attachment to a bone;
an underpass layer of a porous material disposed on a first side of the component for fixed attachment;
at least one strut on the underpass layer, the at least one strut having a first surface contacting the underpass layer and a second surface opposite the first surface, the at least one strut comprising a non-porous material, wherein the porous material in the underpass layer is shaped into at least one strip extending perpendicular to a longitudinal direction of the plurality of one or more struts; and
an additional layer of the porous material filling a respective volume adjacent the at least one strut, the additional layer extending from a first side of the underpass layer to a predetermined height equal to or above a height of the second surface of the at least one strut.

* * * * *